United States Patent
Stöckel et al.

(10) Patent No.: US 6,312,454 B1
(45) Date of Patent: Nov. 6, 2001

(54) STENT ASSEMBLY (75) Inventors: Dieter Stöckel, Los Altos; Thomas Duerig, Fremont; Janet Burpee, Santa Clara, all of CA (US)

(73) Assignee: Nitinol Devices & Components, Fremont, CA (US)

( * ) Notice: Subject to any disclaimer, the term of this patent is extended or adjusted under 35 U.S.C. 154(b) by 0 days.

(21) Appl. No.: 08/662,472

(22) Filed: Jun. 13, 1996

(51) Int. Cl.$^7$ ........................................ A61F 2/06
(52) U.S. Cl. .................. 623/1; 623/12; 606/191; 606/198; 604/104
(58) Field of Search .................. 623/1, 12; 606/191, 606/198; 604/104, 107

(56) References Cited

U.S. PATENT DOCUMENTS

| | | | |
|---|---|---|---|
| 3,868,956 | * | 3/1975 | Alfidi et al. ............... 128/899 |
| 4,994,071 | * | 2/1991 | MacGregor ............... 606/194 |
| 5,064,435 | * | 11/1991 | Porter ............... 623/12 |
| 5,078,736 | * | 1/1992 | Behl ............... 623/1 |
| 5,290,305 | * | 3/1994 | Inoue ............... 623/1 |
| 5,514,176 | | 5/1996 | Bosley, Jr. |
| 5,534,007 | * | 7/1996 | St. Germain et al. ............... 606/191 |
| 5,632,772 | * | 5/1997 | Alcime et al. ............... 623/1 |
| 5,681,345 | * | 10/1997 | Euteneuer ............... 623/1 |

FOREIGN PATENT DOCUMENTS

| | | |
|---|---|---|
| 0119688 | 9/1984 | (EP) . |
| 0 437 795 A1 | 7/1991 | (EP) . |
| 0 521 595 A2 | 1/1993 | (EP) . |
| 0696447 | 2/1996 | (EP) . |
| WO 9219310 | 12/1992 | (WO) . |
| Wo 95/24236 | 9/1995 | (WO) . |

* cited by examiner

*Primary Examiner*—Paul B. Prebilic
(74) *Attorney, Agent, or Firm*—Dean Garner (57) ABSTRACT

A stent assembly comprises a stent whose configuration can change between a transversely compressed state for delivery into a lumen in a human or animal body, and a relaxed state in which in use the stent contacts the lumen to support it. The stent is positioned in a delivery device and constrained by it in its transversely compressed state. The delivery device comprises a tubular member formed from a shape memory alloy and can be fitted to or within a catheter for delivery of the stent through a lumen.

11 Claims, 6 Drawing Sheets

STENT ASSEMBLY

BACKGROUND TO THE INVENTION

This invention relates to a stent assembly which comprises a stent and a delivery device for the stent, to a catheter assembly which includes the stent assembly, and to a method of disposing a stent in a lumen in a human or animal body.

Stents are used in lumens in a human or animal body, including for example blood vessels, bile ducts, urinary tracts and so on. When properly positioned in a lumen, a stent can contact the wall of the lumen to support it or to force the wall outwardly.

Stents can be made from a material which enables the stent to be compressed transversely elastically so that they can then recover outwardly when the compressing force is removed, into contact with the wall of the lumen. Such stents are often referred to as "self-expanding stents". The enhanced elastic properties available from shape memory alloys as a result of a transformation between martensite and austenite phases of the alloys make them particularly well suited to this application. The nature of the superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document. A principal characteristic of shape memory alloys involves an initial increase in strain, approximately linearly with stress. This behaviour is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

Non-linear superelastic properties can be introduced in a shape memory alloy by a process which involves cold working the alloy for example by a process that involves pressing, swaging or drawing. The cold working step is followed by an annealing step while the component is restrained in the configuration, resulting from the cold working step at a temperature that is sufficiently high to cause dislocations introduced by the cold working to combine and dislocations to align. This can ensure that the deformation introduced by the cold work is retained.

The properties of shape memory alloys can also involve thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase. It is known from U.S. Pat. No. 5,197,978 to make use of the thermally induced change in configuration of an article made from a shape memory alloy in a stent.

Stents can also be made from materials that do not exhibit the shape memory properties of shape memory alloys. Examples include certain stainless steels.

Self-expanding stents are commonly delivered to a desired location in a lumen using a catheter, in which the stent is constrained in a transversely compressed configuration, from which it can expand when released from the catheter to contact the wall of the lumen. Catheters formed from polymeric material are commonly used, for example because of their flexibility which facilitates steering the catheter through a lumen, and also for reasons of cost. It has been found in certain circumstances that a stent constrained within a catheter formed from a soft polymeric material can become embedded in the internal wall of the catheter due to elastic forces exerted by the stent as it attempts to expand, to an extent which can make it difficult to discharge the stent from the catheter. A stent constraint which is formed from a polymeric material, and which has the physical characteristics appropriate to constrain the stent, will generally have a large wall thickness, making it inflexible and bulky.

SUMMARY OF THE INVENTION

The present invention provides a stent assembly which includes a tubular delivery device formed from a shape memory alloy in which the stent can be located, the wall of the delivery device being configured to facilitate flexing of the tube in bending deformation.

Accordingly, in one aspect, the invention provides a stent assembly which comprises:

(a) a stent whose configuration can change between a transversely compressed state for delivery into a lumen in a human or animal body, and a relaxed state in which in use the stent contacts the lumen to support it, and (b) a delivery device which can be fitted to or within a catheter for delivery of the stent through a lumen, which comprises a tubular member formed from a shape memory alloy, the stent being positioned in the delivery device and constrained by it in its transversely compressed state.

In another aspect, the invention provides a method of disposing a stent in a lumen in a human or animal body, which comprises:

(a) transversely compressing the stent, (b) locating the stent in a delivery device which comprises a tubular member formed from a shape memory alloy, the stent being positioned in the delivery device and constrained by it in its transversely compressed state, (c) moving the delivery device with the stent contained within it to a desired location in the human or animal body by means of an elongate member having distal and proximal ends, the delivery device and stent being fitted to or contained in the elongate member at or towards the distal end thereof, and (d) discharging the stent from within the delivery device.

The present invention provides a construction in which a stent can be constrained in a transversely compressed configuration for delivery in a lumen by means of an elongate member, especially a hollow member such as a catheter. A suitable catheter might be formed from, for example, a polymeric material, which might be deformed by the stent if located directly in the stent and constrained by contact with the inner wall of the catheter. This facilitates discharge of the stent from the catheter.

The stent can be discharged from the delivery device either by advancing the stent forward with respect to the delivery device, or by withdrawing the delivery device from the site at which the stent is to be deployed and with respect to the stent.

The constraint provided according to the present invention has the advantage of being thin-walled and flexible in bending, while also having sufficient radial stiffness to be able to withstand the forces exerted by the stent as it attempts to recover outwardly, even when these forces are applied over a long period of time at temperatures above body temperature.

Preferably, the stent is formed from a shape memory alloy. Preferably, the shape memory alloy has been treated so that it is superelastic. The superelastic properties are employed by the stent in its change of configuration between compressed and relaxed states. An appropriate treatment can involve a combination of cold working (for example by swaging, drawing or, in particular by mandrel expansion) and heat treatment at a temperature that is less than the recrystallisation temperature of the alloy while the stent is constrained in the configuration resulting from the cold work. A plurality of the cold work and heat treatment steps can be used. The stent can then be deformed towards the configuration of the stent in its compressed state, the deformation being recoverable, substantially elastically. In this way, deformations of up to 8% strain can be imparted and recovered substantially elastically.

Alloys from which the stent can be made include Ni—Ti based alloys, especially Ni—Ti binary alloys such as those in which the nickel content is at least about 50 atomic percent (hereinafter at. %), preferably at least about 50.5 at. %. The nickel content will usefully be less than about 54 at. %, preferably less than about 52 at. %. The method can also be performed on other Ni—Ti based alloys, including alloys with ternary and quaternary additions. Examples of elements that can be incorporated in the alloy include Fe, Co, Cr, Al, Cu and V. Added elements can be present in amounts up to about 10 at. %, preferably up to about 5 at. %.

When the stent is formed from a shape memory alloy, the alloys of the stent and of the delivery device are preferably selected so that the difference between their $A_f$ temperatures (the temperatures at which the transformations from martensite phase to the austenite phase are complete) temperatures is less than about 40° C. In this way, the variation in flexibility of the stent and the delivery device with temperature can both be appropriate for delivery into a body lumen.

Preferably, the wall of the delivery device is configured to facilitate flexing of the tubular member in bending deformation. For example, at least one slot might be formed in the tubular member of the delivery device, extending part way around the device. The slot or slots can be circumferential, lying in a plane that is substantially perpendicular to the axis of the device. The slot or slots can be lie at an angle to that plane. Non-straight slots can be included; for example, one, some or all of the slots might have a chevron configuration.

The slots can extend through an arc of at least about 150° or more. Other configurations might be used, for example with slots extending through an angle of at least about 75°, or at least about 90°, or preferably at least about 120°. The slots might not extend through more than about 280°, preferably not more than about 240°, more preferably not more than about 170°, for example not more than about 150°. Preferably, a series of such slots is provided in the wall of the tubular member. When there are several slots in the wall of the tubular member, they will preferably be offset circumferentially with respect to one another, especially when the slots are relatively short. For example, one of the slots might be offset by about 90° with respect to its adjacent slot. Preferably, the arrangement of slots along the delivery device is arranged in a substantially regular pattern, for example alternating with the non-broken section of the wall of the tubular member at 0° and 90°. The slots might however be arranged in another pattern, for example adjacent slots being offset by less than about 90° along the device.

The tubular member of the delivery device might have at least one helical slot formed in its wall, extending along the device. A plurality of slots might be formed in the wall of the tubular member, for example in axially separated sections of the member, or overlapping in a section of the tubular member but radially offset relative to one another.

Preferably, the tubular member of the delivery device can have a closed cross-section, at least over a portion of its length. The closed cross-section may be one that is taken perpendicular to the axis of the assembly or, in some constructions, at an angle other than 90° to that axis. More preferably, the tubular member is formed from an article which has a closed cross-section over its entire length so that it is a tube. This has the advantage of ease of controlled manufacture with desired physical characteristics. An alternative construction of device involve formation from a sheet, for example by rolling it to form the tubular member.

Preferably, the delivery device is longer than the stent that is to be delivered by it. Preferably, the difference in length between the stent and the delivery device is at least about 2 mm, more preferably at least about 4 mm, especially at least about 6 mm. Preferably, the difference is not more than about 15 mm, more preferably not more than about 10 mm. Preferably, the ratio of the length of the delivery device to that of the stent is not more than about 1.5, more preferably not more than about 1.2.

Preferably, the stent assembly includes means for facilitating release of the stent from within the delivery device. For example, one of the contacting surfaces of the stent and the delivery device might be coated with a material which reduces friction effects between those surfaces.

Preferably, the wall thickness of the stent is not more than about 1 mm, more preferably not more than about 0.5 mm, especially not more than about 0.3 mm. Preferably, the wall thickness is at least about 0.1 mm, more preferably at least about 0.2 mm.

Preferably, the maximum transverse dimension (which will be its diameter when the stent is in its relaxed configuration) of the stent (which will be its diameter when the stent has a circular cross-section) is not more than about 15 mm, more preferably not more than about 5 mm. Preferably, its minimum transverse dimension is at least about 0.5 mm, more preferably at least about 1 mm. It will be understood that these are the dimensions of the stent prior to any subsequent expansion steps that might be used when the stent is formed from a shape memory alloy which is to be expanded as part of its treatment.

The configuration of the delivery device will be selected so that it can properly contain the stent, and withstand forces exerted by the stent prior to discharge from the device, such as for example the elastic recovery forces against which the stent is held under constraint. Preferably, the delivery device has the minimum wall thickness necessary to satisfy these criteria.

In a further aspect, the invention provides a catheter assembly for delivering a stent through a lumen in a human or animal body, which comprises a catheter having a distal end and a proximal end, and a stent assembly as discussed above that is fitted to or within the catheter towards the distal end thereof.

The stent assembly can be fitted within the bore of the catheter, with the end of the stent assembly substantially flush with the end of the catheter or recessed from that end. The stent assembly can extend beyond the end of the catheter, for example to the extent that the stent assembly is effectively provided on the end of the catheter.

Preferably, the catheter comprises a polymeric material, at least in the region thereof in which the stent assembly is located. Suitable polymeric materials include polyolefins. The use of a polymeric material at least in the region of the catheter occupied by the stent assembly has the advantage of facilitating flexing of the catheter, which can be particularly important in the distal region when it is to be steered through lumens in the body of a patient to deliver the stent to a desired location.

DESCRIPTION OF PREFERRED EMBODIMENTS

Figure 1:
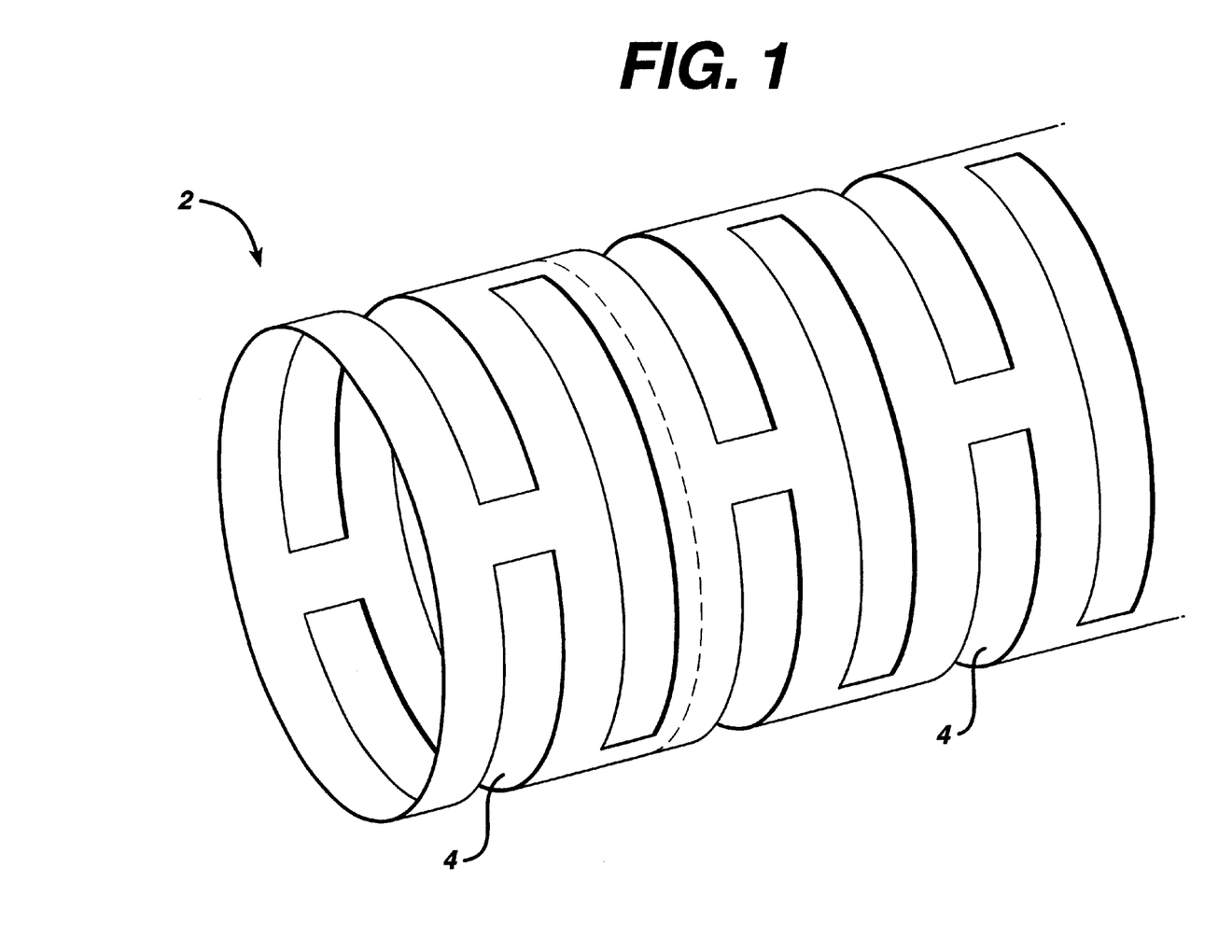
FIG. 1 is an isometric view of a delivery device for use in a stent assembly according to the invention.

The delivery device shown in FIG. 1 is intended for use in a stent assembly which also includes a stent. The stent can be formed from a nickel titanium shape memory alloy containing about 50.8 at. % nickel. The stent can have shape memory properties imparted to it by an expansion step in which it is expanded transversely from its configuration as machined, for example using one or more mandrels. The amount of expansion will depend on the degree to which the stent is required to deform elastically for insertion into a lumen and then to expand elastically into contact with the lumen, and optionally to expand it. The nature of the treatment of the stent to give it appropriate elastic properties will be apparent to a person skilled in the art. An appropriate technique can comprise a combination of one or more expansion steps (for example using drawing or swaging, especially using one or a plurality of mandrels) which result in cold working the alloy. After the or each cold working step, the alloy can be subjected to a heat treatment while restrained in the configuration resulting from the cold working step at a temperature that is less than the recrystallisation temperature of the alloy. As a result of the cold working and heat treatment steps, the stent is capable of being deformed elastically to strains of up to about 8% or more.

The stent is configured to facilitate its changes in configuration, involving transverse compression and expansion, by being formed with a plurality of openings into it. The openings can be created by forming the stent from wire. Preferably, however, the stent is formed from a tube and the openings are created by cutting the tube, for example using a YAG laser operating in an atmosphere of an oxygen/argon mixture.

A stent which might be incorporated in the stent assembly of the invention might be made from a tube with an external diameter of about 2.5 mm and a wall thickness of about 0.25 mm. Longitudinally extending slits of length about 2.5 mm spaced about 0.6 mm apart can be cut in the tube in lines extending along the tube that are spaced about 0.2 mm apart around its circumference, the slits in one line being offset relative to slits in adjacent lines. The width of each slit is about 0.15 mm. The length of the stent is about 15 mm.

The delivery device 2 shown in FIG. 1 is made from the same alloy as the stent. It too is formed from a tube by cutting a pattern into it. The pattern cut into the delivery device comprises a plurality of circumferential slots 4 extending through an arc of about 150° around the tube, each slot being offset circumferentially around the tube relative to the adjacent slot by about 90°. The orientation of the slots therefore alternates along the tube.

The delivery device is 20 mm long and has a wall thickness of about 0.1 mm.

Prior to use, a stent is compressed transversely and fitted into the delivery device 2 which prevents expansion of the stent during its delivery to a desired location in a body. The stent can be fitted into the delivery device in this way for example by means of a tapered sleeve similar to a funnel, by which the stent is compressed as it is forced through it. The assembly comprising the stent and the delivery device can be flexed easily, as a result in part of the openings cut into the stent and, in particular, the delivery device.

The stent can be delivered to a desired location in a human or animal body by means of a catheter passed along lumens in the body. Suitable catheters are often formed from polymeric materials which are flexible to enable them to negotiate junctions between the lumens and the tortuous pathways presented by the lumens. For many applications, the catheter will be constructed so that it is as flexible as possible, consistent with having sufficient longitudinal rigidity to be manipulated.

Figure 2:
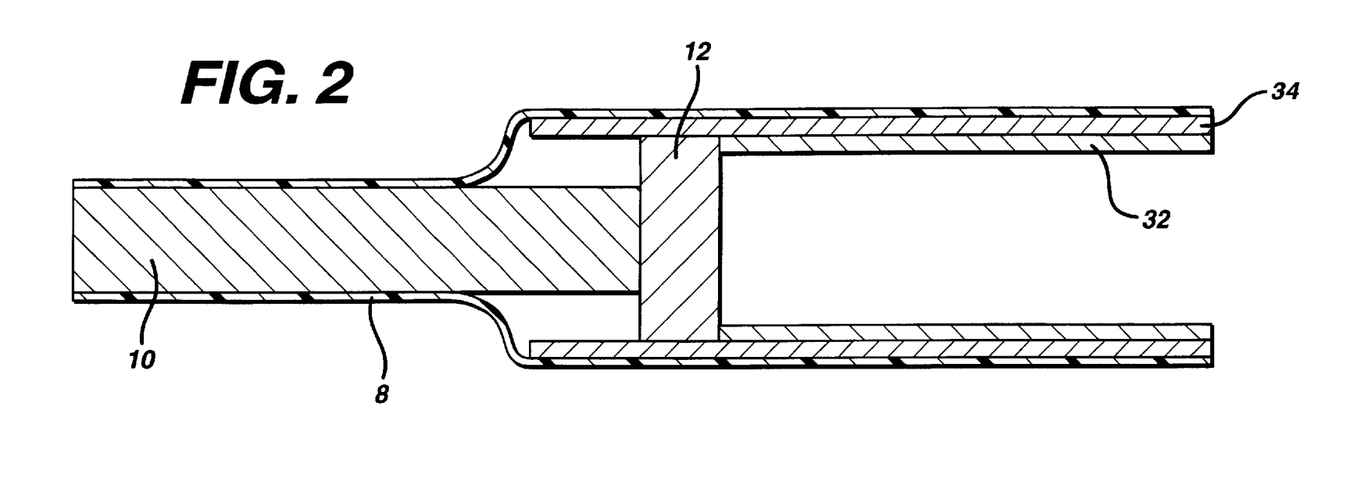
FIGS. 2 and 3 are side views, partially in section, through catheter assemblies comprising a stent assembly employing a delivery device as shown in FIG. 1, a stent and a catheter.

As shown in FIG. 2, a stent 32 with its delivery device 34 are positioned in a catheter 8, at the distal end thereof. The delivery device fits within the catheter, the end of the delivery device being flush with the end of the catheter. The use of a delivery device in the catheter can avoid deformation of the catheter by the stent as a result of the outward force exerted by the stent as it attempts to recover towards the configuration from which it was compressed transversely. This factor can be exacerbated when the polymeric material for the catheter is selected for its flexibility since the desired flexibility can often be accompanied by softness.

The stent is discharged from the delivery device and the catheter once the catheter has been directed through one or more lumens (such as blood vessels) to an appropriate location. The stent is discharged by application of force along the catheter, against the stent relative to the catheter and delivery device, generally as known for the discharge of stents from catheters. This can be achieved by means of a wire 10 which extends through the catheter, which has a plunger 12 on its distal end of appropriate dimensions to ensure that an axially applied force can be imparted to the stent. Preferably, the wire is formed from a shape memory alloy which has been treated so that it exhibits enhanced elastic properties.

Figure 3:
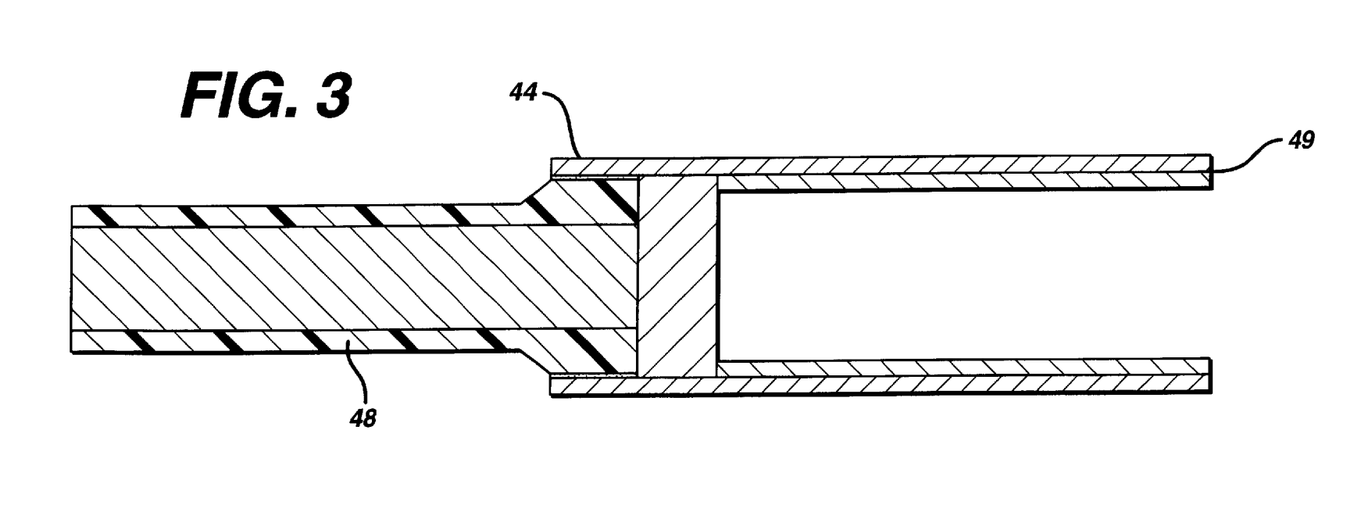

In the construction shown in FIG. 3, the delivery device 44 is provided on the end 49 of the catheter 48 so that the stent assembly extends beyond the end of the catheter. The stent 42 is provided within the delivery device 44 beyond the end of the catheter. The delivery device is located on the catheter by means of an adhesive.

Figure 4A:
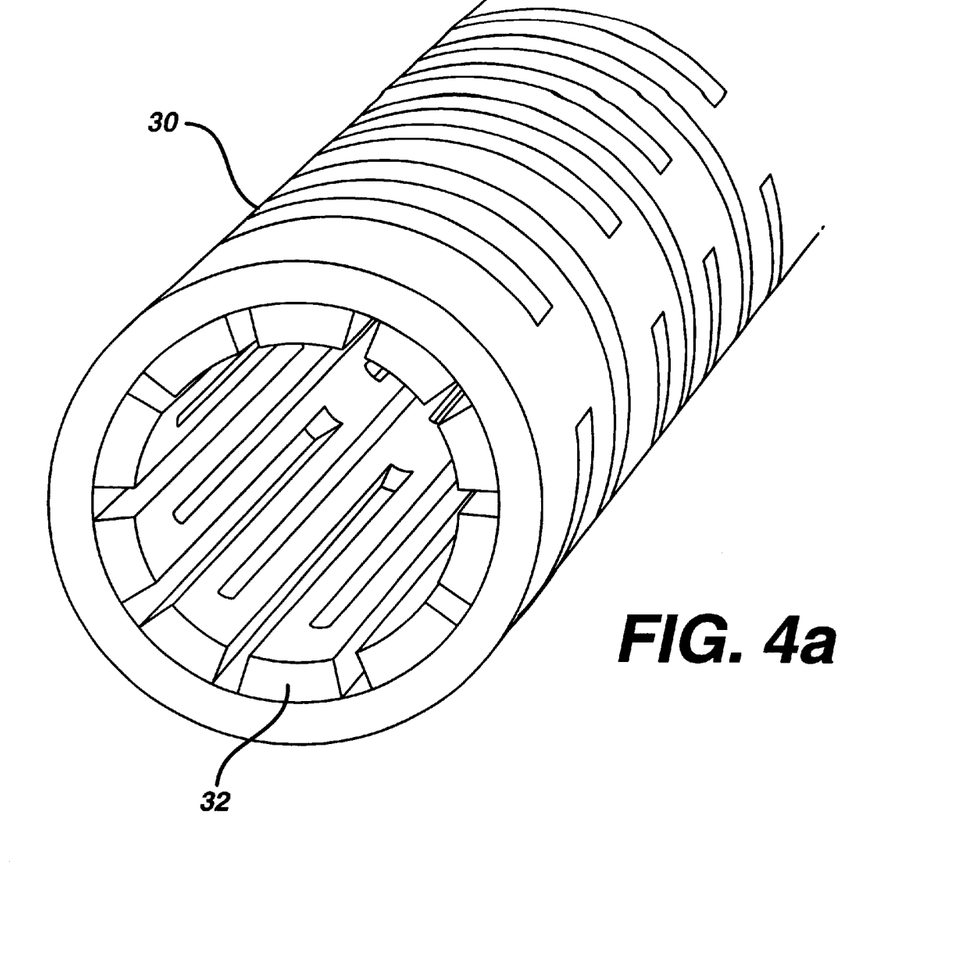
FIGS. 4a, 4b, 5a, 5b, 6a, and 6b are (a) isometric views and (b) in section showing the discharge of a stent from the delivery device.
Figure 4B:
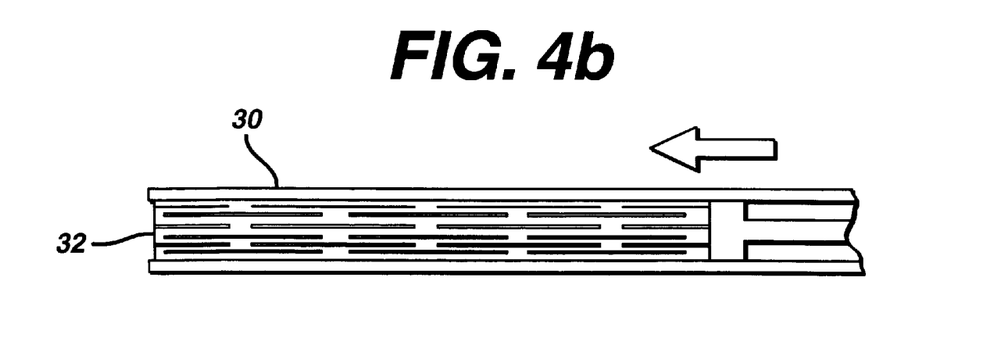
Figure 5A:
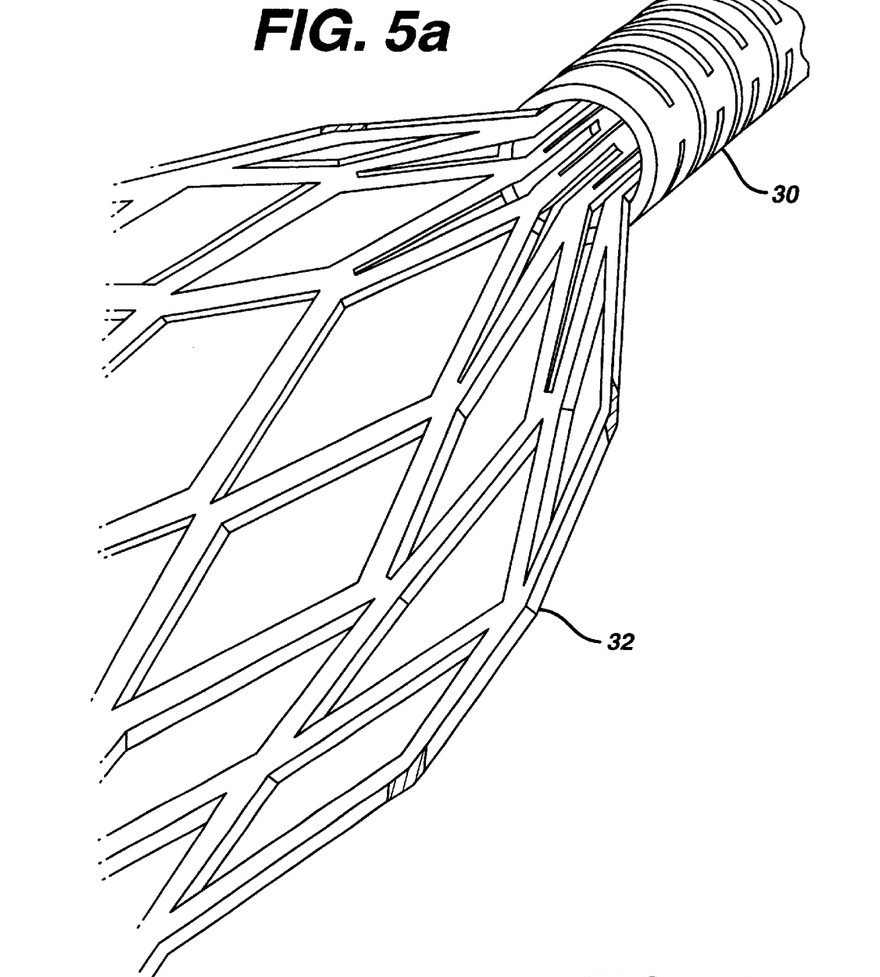
Figure 5B:
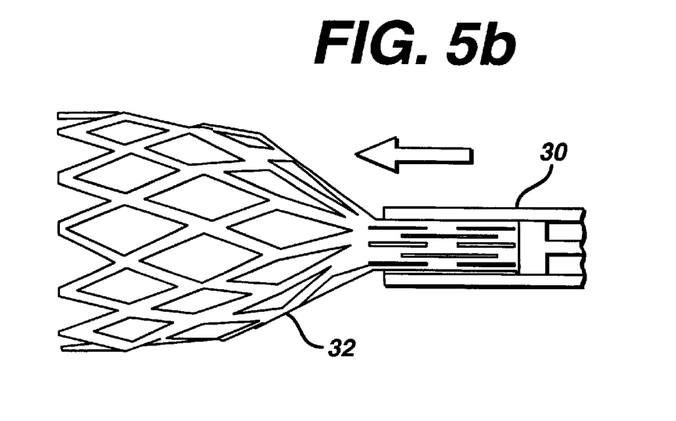
Figure 6A:
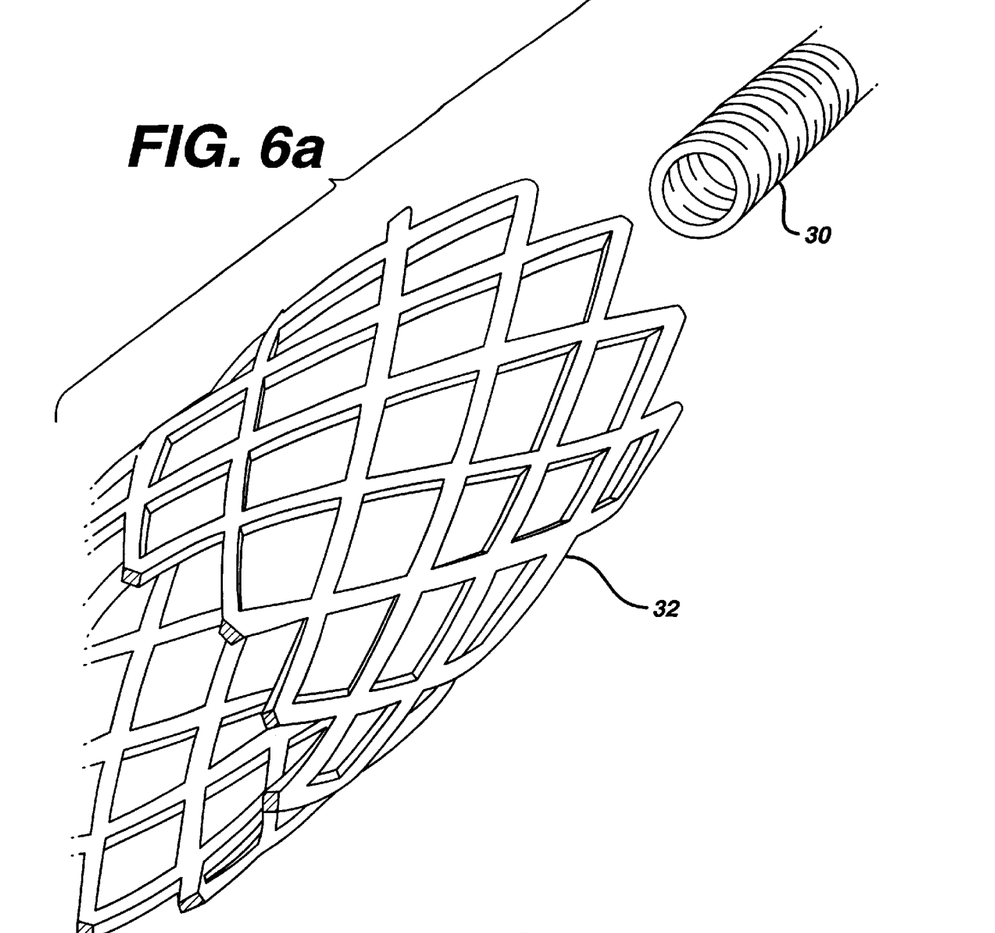
Figure 6B:
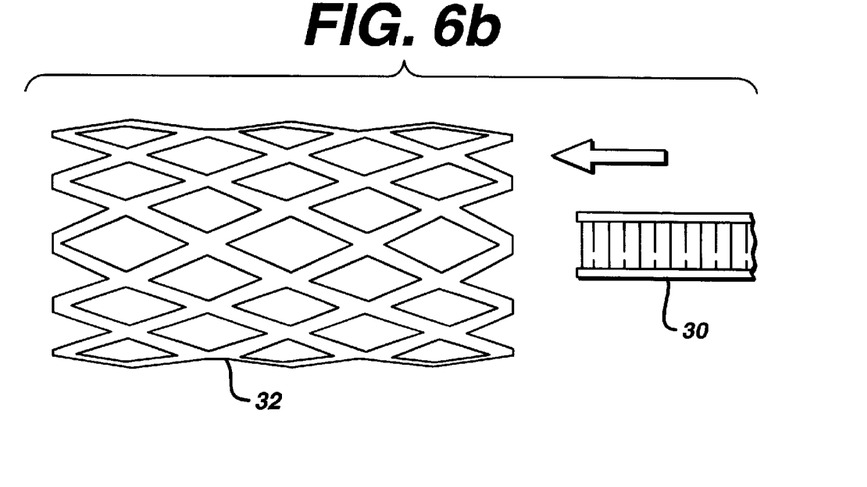

FIG. 4a and 4b show in isometric and sectional elevation views respectively a delivery device 30 of the type described above in relation to FIG. 1 which has a stent 32 located inside it towards an end thereof. On application of axial force to the stent by means of a wire 33 extending through the delivery catheter and a plunger 34 (as in the assembly shown in FIG. 2), the stent 32 can be discharged from the delivery device 30. Delivery of the stent from its delivery device is shown FIGS. 5a and 5b (again showing isometric and sectional elevation views respectively), as the stent 32 protrudes from the delivery device 30, it is released from the constraint provided by the delivery device and expands transversely. FIGS. 6a and 6b show in isometric and sectional elevation views respectively the stent 30 completely released from the delivery device 32, in its transversely expanded configuration. When discharged into a lumen such as a blood vessel, the discharged stent will attempt to recover outwardly towards the configuration shown in FIGS. 6a and 6b, applying an outward force to the wall of the lumen.

Figure 7:
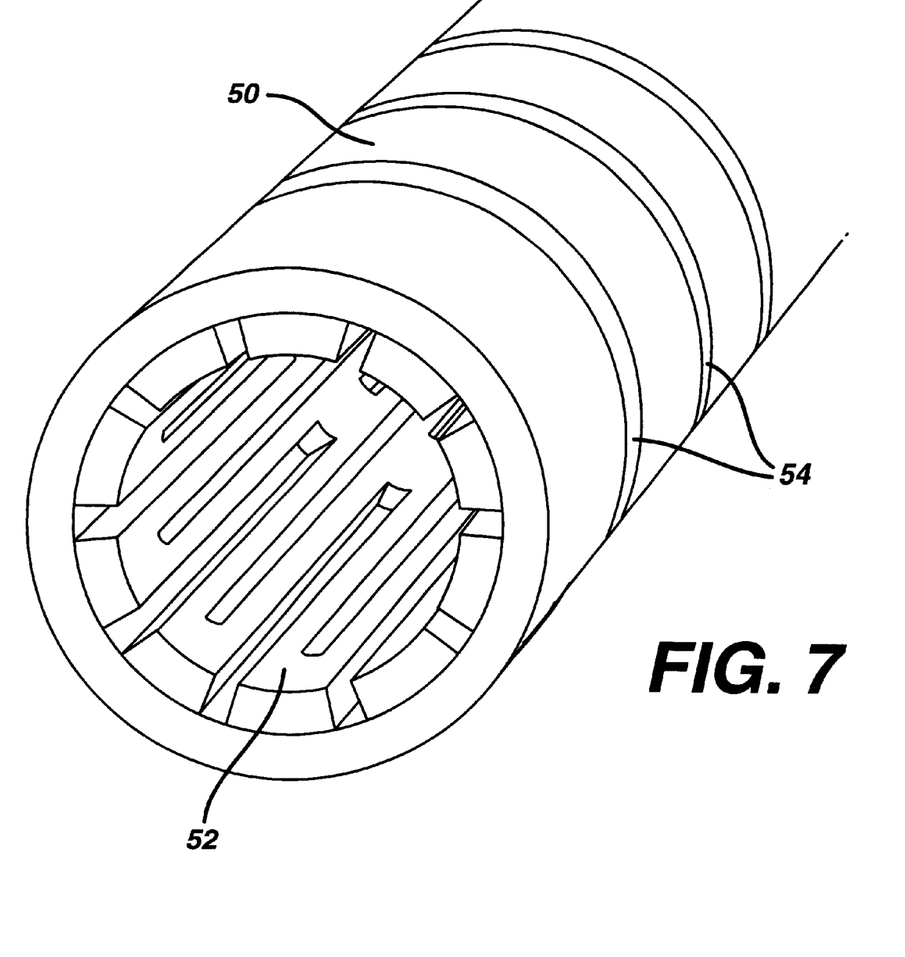
FIG. 7 is an isometric view of another embodiment of delivery device with a stent within it.

FIG. 7 shows a delivery device 50 which has a stent 52 located inside it towards an end thereof. The delivery device has a helical slot 54 formed in its wall.

What is claimed is:

1. A stent assembly which comprises:
   (a) a stent whose configuration can change between a transversely compressed state for delivery into a lumen in a human or animal body, and a relaxed outwardly expanded state in which in use the stent contacts the lumen to support it, the stent is formed from a superelastic alloy which exhibits changes in phase between martensite and austenite phases, and
   (b) a delivery device which can be fitted within a catheter for delivery of the stent through a lumen by way of the catheter, the delivery device comprising a tubular member formed from a superelastic alloy which exhibits changes in phase between martensite and austenite phases, the stent being compressed and inserted into the delivery device, and the delivery device having sufficient radial stiffness to be able to withstand the forces exerted by the stent as the stent attempts to relax outwardly within the delivery device, such that there is substantially no deformation of the delivery device caused by the stent.

2. A stent assembly as claimed in claim 1, in which the wall of the delivery device is configured to facilitate flexing of the tubular member in bending deformation.

3. A stent assembly as claimed in claim 2, in which the tubular member of the delivery device has at least one circumferentially slot formed in its wall, extending part way around the device.

4. A stent assembly as claimed in claim 1, in which the tubular member of the delivery device has at least one helical slot formed in its wall.

5. A stent assembly as claimed in claim 1, in which the tubular member has a closed cross-section, at least over a portion of its length.

6. A stent assembly as claimed in claim 1, in which the delivery device is longer than the stent.

7. A stent assembly as claimed in claim 6, in which the ratio of the length of the delivery device to that of the stent is not more than about 1.5.

8. A stent assembly as claimed in claim 6, in which the ratio of the length of the delivery device to that of the stent is not more than about 1.2.

9. A method of disposing a stent in a lumen in a human or animal body, which comprises:
   (a) transversely compressing the stent,
   (b) locating the stent in a delivery device which comprises a tubular member formed from a shape memory alloy, the stent being positioned in the delivery device and constrained by it in its transversely compressed state,
   (c) moving the delivery device with the stent contained within it to a desired location in the human or animal body by means of an elongate member having distal and proximal ends, the delivery device and stent being fitted to or contained in the elongate member at or towards the distal end thereof, and
   (d) discharging the stent from within the delivery device.

10. A stent delivery system comprising:
    (a) a stent whose configuration can change between a transversely compressed state for delivery into a lumen in a human or animal body, and a relaxed outwardly expanded state in which in use the stent contacts the lumen to support it, the stent is formed from a superelastic alloy which exhibits changes in phase between martensite and austenite phase, and
    (b) a catheter and a delivery device fitted within a distal end of the catheter for delivery of the stent through a lumen by way of the catheter, the delivery device comprising a tubular member formed from a superelastic alloy which exhibits changes in phase between martensite and austenite phases, the stent being compressed and inserted into the delivery device, and the delivery device having sufficient radial stiffness to be able to withstand the forces exerted by the stent as the stent attempts to relax outwardly within the delivery device, such that there is substantially no deformation of the catheter caused by the stent.

11. The system according to claim 10 wherein the distal end of the catheter is made at least partially from a polymeric material.

* * * * *